US00RE39502E

(19) United States
(12) Reissued Patent
Fox et al.

(10) Patent Number: US RE39,502 E
(45) Date of Reissued Patent: Mar. 6, 2007

(54) STABLE PHARMACEUTICAL COMPOSITIONS CONTAINING 7-SUBSTITUTED-3,5-DIHYDROXYHEPTANOIC ACIDS OR 7-SUBSTITUTED-3,5-DIHYDROXYHEPTENOIC ACIDS

(75) Inventors: Michael Fox, Tel Aviv (IL); Ivo Dorossiev, Herzlia (IL)

(73) Assignee: Teva Pharmaceutical Industries Ltd., Petah Tiqva (IL)

(21) Appl. No.: 11/083,366

(22) Filed: Mar. 17, 2005

Related U.S. Patent Documents

Reissue of:
(64) Patent No.: 6,558,659
Issued: May 6, 2003
Appl. No.: 09/829,026
Filed: Apr. 9, 2001

U.S. Applications:
(60) Provisional application No. 06/195,916, filed on Apr. 10, 2000.

(51) Int. Cl.

| | |
|---|---|
| ***A61K 31/74*** | (2006.01) |
| ***A61K 9/48*** | (2006.01) |
| ***A61K 9/20*** | (2006.01) |
| ***A61K 9/14*** | (2006.01) |
| ***A61K 31/425*** | (2006.01) |

(52) U.S. Cl. ..... 424/78.31; 424/451; 424/464; 424/489; 514/367; 514/369

(58) Field of Classification Search ..... 424/78.31, 424/451, 464, 489; 514/937, 369, 367
See application file for complete search history.

(56) References Cited

U.S. PATENT DOCUMENTS

| | | | | |
|---|---|---|---|---|
| 5,030,447 A | * | 7/1991 | Joshi et al. | 514/510 |
| 5,180,589 A | | 1/1993 | Joshi et al. | |
| 5,225,202 A | * | 7/1993 | Hodges et al. | 424/480 |
| 5,273,995 A | | 12/1993 | Roth | |
| 5,582,838 A | | 12/1996 | Rork et al. | |
| 5,627,200 A | * | 5/1997 | Kreutter et al. | 514/367 |
| 5,686,104 A | | 11/1997 | Mills et al. | |
| 5,798,375 A | * | 8/1998 | Tsujita et al. | 514/369 |
| 6,147,090 A | | 11/2000 | DeNinno et al. | |
| 6,207,664 B1 | | 3/2001 | Hayward et al. | |
| 6,245,797 B1 | | 6/2001 | Winokur | |
| 7,030,151 B2 | | 4/2006 | Kerc et al. | |

FOREIGN PATENT DOCUMENTS

| | | |
|---|---|---|
| EP | 1 036 783 | 9/2000 |
| WO | WO 00/35425 | 6/2000 |

OTHER PUBLICATIONS

Araki, Yoshitaka et al. "Enantioselective Total Synthesis of (+)–6–epi–Mevinolin and Its Analogs. Efficient Construction of the Hexahydronaphthalene Moiety by High Pressure–Promoted Intramolecular Diels–Alder Reaction of (R, 2Z, 8E, 10E)–1–[(tert–Butyldimethylsilyl) oxy]–6–methyl–2, 8,10–dodecatrien–4–one", J. Org. Chem. Aug. 8, 1997, vol. 62, No. 16, pp. 5299–5309.

Kollidon Grades, "Polyvinylpyrrolidone for the Pharmaceutical Industry", BASF, May 1986, 19 pages.

Scandinavian Simvastatin Survival Study Group, "Randomised Trial of Cholesterol Lowering in 4444 Patients With Coronary Heart Disease: The Scandinavian Simvastatin Survival Study (4S)", The Lancet, Nov. 19, 1994, vol. 344, No. 8934, pp. 1383–1389.

Witztum, Joseph L., "Drugs Used in the Treatment of Hyperlipoproteinmias", Goodman & Gilman's The Pharmacological Basis of Therapeutics, ($9^{th}$ Edition, 1996), pp. 875–897.

* cited by examiner

*Primary Examiner*—Blessing Fubara
(74) *Attorney, Agent, or Firm*—Kenyon & Kenyon LLP

(57) ABSTRACT

Pharmaceutical compositions that have excellent storage stability even though they include a active component that is susceptible to degradation in an acidic environment are disclosed. The stabilized pharmaceutical composition of the invention includes a ring-opened 7-substituted-3,5-dihydroxyheptanoic or a ring-opened 7-substituted-3,5-dihydroxyheptenoic acid, or a pharmaceutically acceptable salt thereof, as an active component and a stabilizing effective amount of at least one amido-group containing polymeric compound or at least one amino-group containing polymeric compound, or combination thereof; wherein the stabilized pharmaceutical composition does not contain a stabilizing effective amount of another stabilizer or a combination of other stabilizers. The pharmaceutical composition may optionally include one or more pharmaceutically acceptable excipients such as a filler, a disintegrating agent and one or more lubricants such as magnesium stearate to aid compression where a tablet dosage form is desired.

55 Claims, No Drawings

STABLE PHARMACEUTICAL COMPOSITIONS CONTAINING 7-SUBSTITUTED-3,5-DIHYDROXYHEPTANOIC ACIDS OR 7-SUBSTITUTED-3,5-DIHYDROXYHEPTENOIC ACIDS

Matter enclosed in heavy brackets [ ] appears in the original patent but forms no part of this reissue specification; matter printed in italics indicates the additions made by reissue.

CROSS-REFERENCE TO RELATED APPLICATION

This application *is a reissue application for U.S. Pat. No. 6,558,659, issued May 6, 2003, which* claims the benefit of provisional application Ser. No. 60/195,916, filed Apr. 10, 2000, which is incorporated entirely herein by reference.

FIELD OF THE INVENTION

The present invention relates to stabilized pharmaceutical compositions comprising statins, and more particularly to stabilized pharmaceutical compositions containing ring-opened 7-substituted-3,5-dihydroxyheptanoic acids or ring-opened 7-substituted-3,5-dihydroxyheptenoic acids, or pharmaceutically acceptable salts thereof. The present invention also relates to the use of such stabilized pharmaceutical compositions for the treatment of dyslipidemias including hyperlipidemia, hypercholesterolemia and hypertriglyceridemia.

BACKGROUND OF THE INVENTION

Complications of cardiovascular disease, such as myocardial infarction, stroke, and peripheral vascular disease account for about half of the deaths in the United States. A high level of low density lipoprotein (LDL) in the bloodstream has been linked to the formation of coronary lesions that obstruct the flow of blood and can rupture and promote thrombosis. Goodman and Gilman, The Pharmacological Basis of Therapeutics 879 (9th ed. 1996). Reducing plasma LDL levels has been shown to reduce the risk of clinical events in patients with cardiovascular disease and in patients who are free of cardiovascular disease but who have hypercholesterolemia. Scandinavian Simvastatic Survival Study Group, 1994; Lipid Research Clinics Program, 1984a, 1984b. In addition, low levels of high density lipoprotein (HDL) and high levels of triglycerides (TG) are also known to be associated with increased incidence of cardiovascular disease and primary and secondary coronary events including, but not limited to, myocardial infarction.

Statins are currently among the most therapeutically effective drugs available for reducing the level of LDL in the blood stream of a patient at risk for cardiovascular disease. Statins are also known to raise HDL cholesterol levels and decrease total triglyceride levels. Specific examples of statins include, inter alia, compactin, lovastatin, mevastatin, simvastatin, pravastatin, atorvastatin, cerivastatin, itavastatin and fluvastatin. The mechanism of action of statins has been elucidated in some detail. It is believed that statins disrupt the biosynthesis of cholesterol and other sterols in the liver by competitively inhibiting the 3-hydroxy-3-methyl-glutaryl-coenzyme A reductase enzyme ("HMG-CoA reductase"). HMG-CoA reductase catalyzes the conversion of HMG-CoA to mevalonate, which is the rate determining step in the biosynthesis of cholesterol. Consequently, its inhibition leads to a reduction in the rate of formation of cholesterol in the liver.

Pravastatin is the common name of the chemical compound [1S-[1α(βS*,δS*)2α, 6α,8β(R*),8aα]]-1,2,6,7,8,8a-hexahydro-β,δ,6-trihydroxy-2-methyl-8-(2-methyl-1-oxobutoxy)-1-naphthaleneheptanoic acid monosodium salt, disclosed in U.S. Pat. No. 4,346,227 to Terahara et al.

Pharmaceutical compositions that include a medicament that is unstable in an acidic environment have been thought to require a basic excipient to enhance storage stability. For example, pravastatin sodium is an HMG-CoA reductase inhibitor having the structural formula:

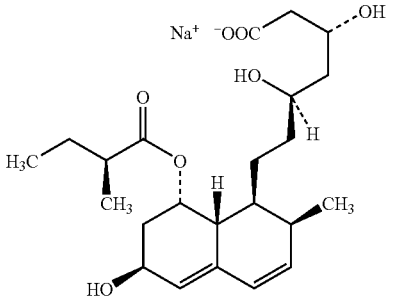

Pravastatin sodium (sold in the U.S. under the trademark PRAVACHOL®) is sensitive to a low pH environment and will degrade to form its lactone and various isomers. Joshi et al. stated in U.S. Pat. No. 5,180,589 that it is necessary to add one or more basifying agents to impart a desired pH of at least 9 to an aqueous dispersion of a pravastatin composition in order to stabilize it. Among the basifying agents disclosed in U.S. Pat. No. 5,180,589 are magnesium oxide, aluminum oxide, alkali metal hydroxides such as sodium hydroxide, potassium hydroxide or lithium hydroxide and alkaline earth metal hydroxides such as calcium hydroxide or magnesium hydroxide. Magnesium oxide is said to be the preferred basifying agent. Thus, the types of basifying agents disclosed in U.S. Pat. No. 5,180,589 as stabilizing agents are inorganic metal oxides and hydroxides, which are generally considered to be strongly alkaline agents.

Atorvastatin calcium, another HMG-CoA reductase inhibitor, is described in U.S. Pat. No. 5,273,995 to Roth. Atorvastatin calcium is [R-(R*,R*)-2-(4-fluorophenyl)-β,δ-dihydroxy-5-(1-methylethyl)-3-phenyl-4-[(phenylamino)-carbonyl]-1H-pyrrole-1-heptanoic acid, hemicalcium salt, and has the following structural formula:

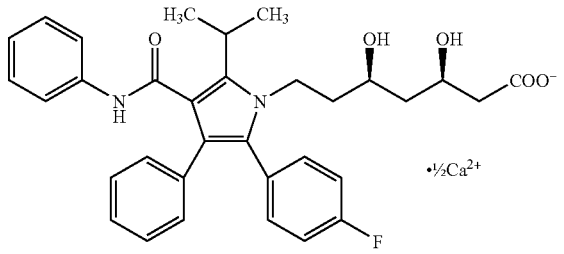

Atorvastatin calcium (sold in the U.S. under the trademark LIPITOR® is susceptible to a low pH environment and can degrade to the corresponding lactone in an acidic environment. Mills et al. have stated in U.S. Pat. No. 5,686,104 that this and similar compounds in an oral pharmaceutical formulation for the treatment of hypercholesterolemia or hyperlipidemia are stabilized by combination with at least one basic inorganic pharmaceutically acceptable calcium, magnesium, aluminum or lithium salt. Examples of these salts are calcium carbonate, calcium hydroxide, magnesium carbonate, magnesium hydroxide, magnesium silicate, magnesium aluminate, aluminum magnesium hydroxide or lithium hydroxide. Calcium hydroxide is disclosed as the preferred alkaline earth stabilizing agent. Thus, as in U.S. Pat. No. 5,180,589, the stabilizing agents disclosed in U.S. Pat. No. 5,686,104 are basic inorganic pharmaceutically acceptable salts.

WO 00/35425 discloses the stabilization of an HMG-CoA reductase inhibitor in a solid formulation with a buffering agent. Among the buffering agents disclosed in WO 00/35425 are sodium or potassium citrate, sodium phosphate, dibasic sodium phosphate, calcium carbonate, hydrogen phosphate, phosphate, sulphate, sodium or magnesium carbonate, sodium ascorbinate, benzoate, sodium or potassium hydrogen carbonate, lauryl sulphate, or mixtures of such buffering agents. Among the HMG-CoA reductase inhibitors disclosed in WO 00/34525 are atorvastatin, pravastatin, fluvastatin and cerivastatin, which are said to be particularly sensitive to an acidic environment in which hydroxy acids are degraded into the corresponding lactone.

As used herein, the term "dyslipidemia" refers to an abnormal level of one or more of total cholesterol (Total-C), low density lipoprotein cholesterol (LDL-C), high density lipoprotein cholesterol (HDL-C), triglycerides (TG), apolipoprotein B (Apo B), apolipoprotein A (Apo A), very low density lipoprotein cholesterol (VLDL-C), and intermediate density lipoprotein cholesterol (IDL-C). By "abnormal" is meant a level generally accepted by the relevant medical community as an undesirable level, which may be higher or lower than desirable, and which may be beneficially adjusted by treatment of a patient with a stabilized statin composition as disclosed herein. Guidelines for the detection, evaluation and treatment of dyslipidemias are promulgated by the National Institute of Health's National Cholesterol Education Program ("NCEP"). The NCEP guidelines suggest when treatment with therapeutic agents such as the statin compounds disclosed herein, are indicated for the treatment of a dyslipidemia such as hypercholesterolemia. Initiation of treatment with a statin compound, in accordance with the NCEP guidelines depends on numerous factors. Among such factors are included abnormal levels of one or more of Total-C, LDL-D, TG, Apo B, Apo A, VLDL-C and IDL-C; familial history of cardiovascular disease or event; prior cardiovascular disease; and, prior occurrence of an acute cardiovascular event, such as myocardial infarction, etc.

By "therapeutically effective amount" as used herein is meant an amount of active component in the stabilized pharmaceutical compositions of the present invention which is effective to beneficially treat a dyslipidemia.

The term "dyslipidemia" thus encompasses "hyperlipidemia", "hypercholesterolemia" and "hypertriglyceridemia" which terms as used herein refer to abnormally high levels of one or more of Total-C, LDL-C, TG, Apo B, VLDL-C and IDL-C. Thus, the term "dyslipidemia" includes all of the dyslipidemias classified by the Frederickson Classification System, including Frederickson Type I hyperlipidemia, Frederickson Types Ia and IIb primary hypercholesterolemia, Frederickson Type IV hypertriglyceridemia, Frederickson Type III dysbetaliproteinemia, and Frederickson Type V hyperlipidemia.

By "stabilized pharmaceutical composition" as used herein is meant that after storage for six months at 40° C. and 75% relative humidity, no more than about 10%, preferably no more than about 5%, and more preferably, no more than about 1% by weight of the active component initially present in the composition degrades into the corresponding lactone.

By "stabilizing effective amount" as used herein is meant an amount by weight of a stabilizing compound present in the pharmaceutical composition which is effective to provide a stabilized pharmaceutical composition.

By "stabilizing effective amount of another stabilizer or a combination of other stabilizers" as used herein is meant an amount of a stabilizing compound or combination of stabilizing compounds, other than the amido-group containing polymeric stabilizing compound or compounds as used in the pharmaceutical compositions of the subject invention, which would provide a stabilized pharmaceutical composition as defined herein. Thus, the present invention is not meant to be construed as excluding compounds that may provide some stabilizing effect, but only to exclude a stabilizing effective amount of one or more of such compounds As disclosed hereinabove, other such stabilizing compounds include, for example, inorganic alkaline and alkaline earth metal salts, oxides and hydroxides as disclosed, for example, in U.S. Pat. No. 5,180,589; U.S. Pat. No. 5,686,104, and buffering agents as disclosed, for example, in WO 00/34525.

By "amido-group containing polymeric compound" as used herein is meant a pharmaceutically acceptable polymeric compound containing, either in a pendant group attached to the polymer backbone, or as a component of the polymer backbone, an amido group, i.e., a group having the formula:

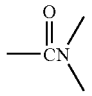

wherein the carbon atom is bonded to another atom and the nitrogen atom is bonded to two other atoms. The term "amido-group containing polymeric compound" is meant to include combinations of different amido-group containing polymeric compounds. Preferred amido-group containing polymeric compounds are those in which nitrogen and carbon are covalently bonded to atoms other than hydrogen. By "tertiary amide group" as used herein is meant an amido-group in which nitrogen is covalently bonded, not including its bond to the carbonyl group, to two atoms neither of which is hydrogen.

By "amino-group containing polymeric compound" as used herein is meant a pharmaceutically acceptable polymeric compound containing, either in a pendant group attached to the polymer backbone, or as a component of the polymer backbone, an amino group, i.e., a group having the formula:

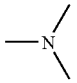

wherein the nitrogen atom is bonded to three other atoms. The term "amino-group containing polymeric compound" is meant to include combinations of different amino-group containing polymeric compounds." Preferred amino-group containing polymeric compounds are those in which the nitrogen atom is covalently bonded to atoms other than hydrogen. Particularly preferred amino-group containing polymeric compounds are those in which the amino group is quaternized, in which case, the amino-group containing polymeric compounds can be equivalently described an a quaternary ammonium salt group containing polymeric compound. The agent used to quaternize the amino group is not critical. Methyl chloride is a preferred quaternizing agent, however, any chemical reagent which is pharmaceutically acceptable and which forms a quaternary ammonium salt by reaction with a tertiary amino group may be used. As examples of quaternizing agents may be mentioned, without limitation, $C_1$–$C_3$ straight or branched chain alkyl halides, phosphates, carbonates, or sulfates; $C_7$–$C_{10}$ aralkyl halides, phosphates or sulfates, and mixtures thereof. Examples of preferred quaternizing agens include but are not limited to methyl chloride, benzyl chloride, diethyl sulfate, dimethyl carbonate, trimethyl phosphate, dimethyl sulfate or mixtures thereof. By "tertiary amino group" as used herein is meant an amino group in which nitrogen is covalently bonded three atoms none of which are hydrogen.

By "aqueous dispersion" as used herein in reference to measurement of the pH of the stabilized pharmaceutical compositions of the present invention is meant an amount of a stabilized pharmaceutical composition of the present invention disintegrated in an amount of deionized water sufficient to provide a concentration of active component of about 1 mg/ml

SUMMARY OF THE INVENTION

In one aspect, the present invention is directed to a stabilized pharmaceutical composition for the treatment of dyslipidemia, comprising as an active component, at least one ring-opened 7-substituted-3,5-dihydroxyheptanoic acid or ring-opened 7-substituted-3,5-dihydroxyheptenoic acid, or a pharmaceutically acceptable acid salt thereof, and a stabilizing effective amount of at least one amido-group containing polymeric compound or at least one amino-group containing polymeric compound, or combination thereof; wherein said stabilized pharmaceutical composition does not contain a stabilizing effective amount of another stabilizer or a combination of other stabilizers.

In another aspect, the present invention is directed to a method for the treatment of dyslipidemia, comprising the step of orally administering to a patient in need of such treatment a therapeutically effective unit dosage of a stabilized pharmaceutical composition comprising, as an active component, at least one ring-opened 7-substituted-3,5-dihydroxyheptanoic acid or ring-opened 7-substituted-3,5-dihydroxyheptenoic acid, or a pharmaceutically acceptable acid salt thereof, and a stabilizing effective amount of at least one amido-group containing polymeric compound or at least one amino-group containing polymeric compound, or combination thereof; wherein said stabilized pharmaceutical composition does not contain a stabilizing effective amount of another stabilizer or a combination of other stabilizers..

DETAILED DESCRIPTION OF THE INVENTION

It has surprisingly been found that a stabilized pharmaceutical composition, especially one for the treatment of dyslipidemia, comprising at least one ring-opened 7-substituted-3,5-dihydroxyheptanoic acid or ring-opened 7-substituted-3,5-dihydroxyheptenoic acid or a pharmaceutically acceptable salt thereof, can be made by providing, in the pharmaceutical composition, a stabilizing effective amount of at least one amido-group containing polymeric compound or at least one amino-group containing polymeric compound, or combination thereof, wherein the stabilized pharmaceutical composition does not contain a stabilizing effective amount of another stabilizer or a combination of other stabilizers. Accordingly, in a preferred embodiment, the present invention provides a stabilized solid pharmaceutical formulation for oral administration comprising a ring-opened 7-substituted-3,5-dihydroxyheptanoic acid such as pravastatin or atorvastatin or a ring-opened 7-substituted-3,5-dihydroxyheptenoic acid, or a pharmaceutically acceptable salt thereof, that is a HMG-CoA reductase inhibitor, as an active ingredient, and a stabilizing effective amount of at least one amido-group containing polymeric compound or a stabilizing effective amount of at least one amino-group containing polymeric compound, or combination thereof; wherein the stabilized pharmaceutical composition does not contain a stabilizing effective amount of another stabilizer or a combination of other stabilizers.

The invention is particularly adapted to solid pharmaceutical compositions containing pravastatin or atorvastatin, or a pharmaceutically acceptable salt thereof, as the active component of the composition. Among the most preferred active components are pravastatin sodium and atorvastatin calcium. Pravastatin sodium and atorvastatin calcium are ring-opened 7-substituted-3,5-dihydroxy-heptanoic acids. However, it is to be understood that the pharmaceutical compositions of the subject invention may contain any ring-opened 7-substituted-3,5-dihydroxy-heptenoic acid. Thus, the pharmaceutical compositions of the subject invention may also contain, as an active ingredient, a statin such as compactin (mevastatin), lovastatin, or simvastatin in the ring-opened form; or a pharmaceutically acceptable salt thereof. Therefore, the pharmaceutical composition of the subject invention can include, as an active ingredient, a crystalline salt of simvastatin as disclosed, for example, in EP 1036783A1, the disclosure of which is entirely incorporated herein by reference.

The stabilized pharmaceutical composition of the subject invention can also include as an active ingredient, a ring-opened 7-substituted-3,5-dihydroxyheptenoic acid, or a pharmaceutically acceptable salt thereof. Examples of these active ingredients include, but are not limited to the HMG-CoA reductase inhibitors fluvastatin, cerivastatin and itavastatin; or a pharmaceutically acceptable salt thereof.

The ring-opened 7-substituted-3,5-dihydroxy-heptanoic acid or 7-substituted-3,5-dihydroxyheptenoic acid can be used in the stabilized pharmaceutical compositions of the present invention either as the free acid or as any pharmaceutically acceptable salt thereof. The free acid can be prepared, for example, by hydrolysis of the corresponding lactone form or by treatment of the salt form of the acid with cationic exchange resin and evaporating the water portion. The free acid can be used to form the pharmaceutically acceptable salt form, by conventional methods known in the art. Among preferred pharmaceutically acceptable salts are metal and amine salts. The term "pharmaceutically acceptable metal salt" thus includes, but is not limited to, sodium, potassium, lithium, calcium, magnesium, aluminum, iron, or zinc salts. Such salts may be derived from bases such as sodium hydroxide, potassium hydroxide, lithium hydroxide, calcium hydroxide, 1-deoxy-2-(methylamino)-D-glucitol, magnesium hydroxide, zinc hydroxide, aluminum hydroxide, ferrous or ferric hydroxide, and ammonium hydroxide. The term "pharmaceutically acceptable amine salt" includes, but is not limited to, salts formed by reaction with ammonium hydroxide or organic amine salt or for example methylglucamine, choline, arginine, 1-deoxy-2-(methylamino)-D-glucitol and the like.

The amount of the active ingredient in the stabilized pharmaceutical compositions of the present invention will be a therapeutically effective amount. A therapeutically effective amount will generally be an amount within the range of from about 0.05 to about 70%, and preferably an amount within the range of from about 1 to about 60% by weight of the composition. It is understood that higher or lower weight percentages of the active ingredient may be present in the pharmaceutical compositions.

Also present in the stabilized pharmaceutical compositions of the present invention is a stabilizing effective amount of at least one amido-group containing polymeric compound or a stabilizing effective amount of at least one amino-group containing polymeric compound, or a stabilizing effective amount of a combination of at least one amido-group and at least one amino-group containing polymeric compound.

An amido-group containing polymeric compound is any pharmaceutically acceptable polymeric compound having, either in a pendant group attached to the polymer backbone, or as a component of the polymer backbone, an amido group as defined hereinabove.

Preferred examples of the amido-group containing polymeric compound include, but are not limited to, polyvinylpyrrolidone (PVP), which is represented by the following formula (where n is the number of repeating units):

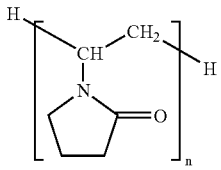

Commercially available polyvinylpyrrolidones have a pH of 3.0–7.0, as measured in a 5% w/v aqueous solution (USP monograph).

Cross-linked polyvinylpyrrolidone, also known, inter alia, as polyplasdone, polyvinyl(poly)pyrrolidone and crospovidone, is a preferred amido-group containing polymeric compound useful in the present invention. Cross-linked polyvinylpyrrolidone has a pH of 5.0–8.0 (1% aqueous suspension, NF). Other polymeric compounds, which are co-polymers containing vinylpyrrolidone monomer units are also useful in the compositions of the subject invention. The term "copolymer" as used herein includes polymers that include two or more distinct monomeric units. An example of such a copolymer containing vinylpyrrolidone monomer units is a copolymer of vinylpyrrolidone monomer units and vinyl acetate monomer units, such as copolyvidone. Polyvinylpyrrolidone, cross-linked polyvinylpyrrolidone, and copolymers containing vinylpyrrolidone monomer units are examples of amido-group containing polymeric compounds in which the amido group is present in a pendant group attached to the polymeric backbone. Also useful in the present invention are amido-group containing polymeric compounds in which the amido group is present in the polymeric backbone. An example of such a polymeric compound is polynoxylin, which is a condensation product of formaldehyde and urea having the following structural formula (where n is the number of repeating units):

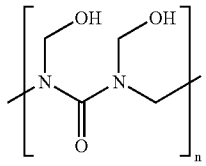

It is to be understood that the amido-group containing polymeric compounds useful to provide stabilized pharmaceutical compositions in accordance with the present invention are not to be construed as limited to the foregoing exemplary polymers. Thus, any pharmaceutically acceptable amido-group containing polymeric compound that provides a stabilized pharmaceutical composition of the present invention may be employed. Such pharmaceutical acceptable amido-group containing polymeric compounds are commercially available. For example, polyvinylpyrrolidone polymers are commercially available, for example, under the trade names KOLLIDON® and PLASDONE®; and, cross-linked polyvinylpyrrolidone polymers are commercially available, for example, under the trade names KOLLIDON CL®, POLYPLASDONE XL®, POLYPLASDONE XL-10® and POLYPLASDONE INF-10®. KOLLIDON® K-30 is a particularly preferred polyvinylpyrrolidone polymer useful in the stabilized pharmaceutical compositions of the present invention.

Polyvinylpyrrolidone, cross-linked polyvinylpyrrolidone, and copolymers containing vinylpyrrolidone monomer units used as the amido-group containing polymeric compound provide the additional advantage in that such compounds also can also function in the stabilized pharmaceutical compositions of the present invention in their conventional roles as excipients; for example, as binders, thickeners and disintegrants. In fact, use of these amido-group containing polymeric compounds can provide the additional advantage of requiring the addition of a lower amount, if any, lubricant to a composition of the subject invention, particularly when the composition is a solid dosage form such as a tablet. Moreover, when such amido-group containing polymeric compounds are used in the pharmaceutical compositions, it has also been found that the need to use separate fillers and disintegrants may be reduced or even eliminated.

The weight percentage of the amido-group containing polymeric compound required to provide a stabilized pharmaceutical composition of the subject invention is generally greater than the weight percentage of the amount of the polymeric compound that would be required to provide its conventional function as an excipient in the pharmaceutical composition such as a solid dosage form adapted for oral administration. Thus, the amido-group containing polymeric compounds are generally used in the pharmaceutical compositions of the subject invention in greater amounts than when used as conventional excipients.

An amino-group containing polymeric compound is any pharmaceutical acceptable polymeric compound having, either in a pendant group attached to the polymer backbone, or as a component of the polymer backbone, an amino group as defined hereinabove.

A preferred amino-group containing polymeric compound is cholestyramine, having the following structural formula where n is the number of repeating units.

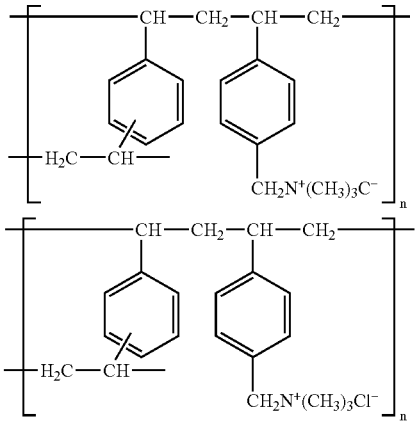

Cholestyramine is thus a copolymer of styrene (vinylbenzene) and divinylbenzene, containing about 2% divinylbenzene. Cholestyramine useful in the stabilized pharmaceutical compositions of the present invention is commercially available from different manufacturers under the tradenames, inter alia, COLESTYRAMINE®, MK-135, and DOWEX 1-X2–Cl. It is understood that the amino-group containing polymeric compounds can be any pharmaceutically acceptable amino-group containing polymeric compounds, or combination thereof.

The pharmaceutical compositions of the present invention will, therefore, generally contain between about 10 to about 99 percent; preferably between about 30 to about 80 percent by weight; and even more preferably, greater than about 30% by weight of the pharmaceutical composition of the amido-group or amino-group containing polymeric compound or combination thereof. Even more preferred yet are percentages of about 40% or greater by weight of the pharmaceutical composition. A particularly preferred percentage of the amido-group or amino-group containing polymeric compound, based on the weight of the pharmaceutical composition, will be greater than 40%.

The pharmaceutical compositions of the present invention may also contain any pharmaceutically acceptable excipient or combination thereof. Conventional pharmaceutical excipients include those which function in a dosage form, for example, as a lubricant, glidant, diluent, binder, disintegrant, carrier, colorant or coating material. Examples of pharmaceutically acceptable excipients include, but are not limited to, lactose, sugar, corn starch, modified corn starch, mannitol, sorbitol, silicon dioxide, and microcrystalline cellulose.

The preferred dosage forms of the stabilized pharmaceutical compositions of the present invention are solid dosage forms adapted for oral administration. However, within the scope of the dosage forms useful for formulating the stabilized compositions of the present invention include suspensions, solutions (drinkable and injectable) and emulsions. Tablet dosage forms are the particularly preferred solid dosage forms of the stabilized pharmaceutical compositions of the present invention. Tablet dosage forms may contain for example, as excipients, any pharmaceutically acceptable lubricant, binder, disintegrant, diluent, carrier, preservative or combination thereof. Solid dosage forms that are not formulated as tablets typically do not need a lubricant component since this is typically added to facilitate manufacture of tablet dosage forms. For the purpose of stable oral preparations of the present invention, pharmaceutically acceptable inert carriers can be either solid or liquid. Among other preferred dosage forms useful for formulating the stabilized pharmaceutical compositions of the present invention include powders, dispersible granules, dispersions, capsules, suspensions and cachets. Conventional methods of manufacturing these preferred dosage forms are employed. Thus, a tablet dosage form can be made, for example, by granulating the active component with or without an excipient, followed by addition of any other excipient(s) and then compression to form a tablet. The tablets are preferably made by direct compression methods as are known in the art. Excipients typically used in tablet dosage forms include carriers, lubricants, binders and fillers that facilitate compacting, shaping, and sizing. Examples of suitable lubricants include magnesium stearate, sodium stearyl fumarate, polyethylene glycol, stearic acid, hydrogenated vegetable oil and talc. Typical amount of lubricant used in a tablet dosage form range from about 0.1 to about 25% and preferably from about 0.25 to about 10% by weight of dosage form. In forming a powder preparation, a finely divided solid carrier is typically employed and is blended with finely divided active ingredient, and then filled into a packet, capsule, or any conventional device for containing the powder. Granular formulations may be similarly packaged. Suspensions or emulsions are obtained by suspending the active component, typically in the form of powder or granules, into a pharmaceutically acceptable liquid carrier which is conventionally adapted for administration orally or parenterally.

Stabilized pharmaceutical compositions of the invention have been produced wherein the only ingredients besides the active component were cross-linked polyvinylpyrrolidone and magnesium stearate. Tablets produced in this manner showed excellent stability in respect to lactone formation upon being subjected to a stability study at 40° C./75% relative humidity for up to six months. However, additional excipients may be beneficially added to obtain improvements in galenic or pharmaceutical parameters such as compressibility, flowability or appearance. Any pharmaceutically acceptable excipient can thus be added to a simple composition containing active component, amido-group containing polymeric compound and lubricant as desired.

An aqueous dispersion of a stabilized statin composition of the present invention will generally exhibit of a pH in the range of about 6.5 to about 10. It is preferred that an aqueous dispersion of a composition of the present invention exhibits a pH of not greater than about 10, preferably not greater than about 8. However, it is also possible to achieve aqueous dispersions of the stabilized statin compositions in accordance with the present invention which have a pH of not greater than about 6.5. Therefore, it is preferred that neither the amido-group containing polymeric stabilizer or amino-group containing polymeric stabilizer, or combination thereof, nor any additional excipient results in a composition in which the pH of an aqueous dispersion thereof is greater than about 10, preferably not greater than about 8. It is particularly preferred that the amount of the amido-group or amino-group containing polymeric stabilizing compound, or combination thereof, does not alter the pH of an aqueous dispersion of a composition of the present invention by more than about one pH unit, relative to the pH of an aqueous dispersion of the same composition not containing the amido-group or amino-group containing polymeric compound or combination thereof.

A particularly preferred embodiment of the present invention provides a stabilized oral pharmaceutical formulation for treatment of dyslipidemia comprising the HMG-CoA reductase inhibitor atorvastatin calcium or pravastatin sodium as the active ingredient in a composition comprising a lubricant such as magnesium stearate and a stabilizing effective amount of an amido-group containing polymeric compound, such as cross-linked polyvinyl pyrrolidone, or a stabilizing effective amount of an amino-group containing polymeric compound, wherein said stabilized pharmaceutical composition does not contain a stabilizing effective amount of another stabilizer or a combination of other stabilizers. The preferred compositions are tablets made by conventional methods of direct compression.

In accordance with the present invention, the pharmaceutical compositions are useful for the treatment of dyslipidemia including, for example, hypercholesterolemia, hyperlipoproteinemia and/or hypertriglyceridemia. While one of ordinary skill in the art will understand that dosages will vary according to the particular requirements and bioavailability of the active ingredient, the indication, age of the patient, and other factors, the compositions of the present invention will generally be administered at a daily dosage of the active ingredient between about 10 to about 500 mg per day, and preferably about 10 mg to about 80 mg per day. As atorvastatin and pravastatin are suitable for once-daily dosing, preferably each unit dosage form will contain between about 10 mg and about 40 mg. In any event, the amount administered per dosage will be a therapeutically effective amount of the active components.

EXAMPLES

The present invention will now be further explained in the following examples. However, the present invention should not be construed as limited thereby. One of ordinary skill in the art will understand how to vary the exemplified preparations to obtain the desired results.

Example 1

A pravastatin formulation in the form of 150 mg tablets having the following composition was prepared as described below.

| Ingredient | Percent By Weight |
|---|---|
| Pravastatin Sodium | 6.67 |
| Crospovidone | 92.33 |
| Magnesium Stearate | 1.00 |

The crospovidone (cross-linked polyvinylpyrrolidone) used in Examples 1–5 and 8 is commercially available from the ISP Company (International Specialty Products), Wayne, N.J. 07470 and is sold under the tradenames POLYPLASDONE XL-10® and POLYPLASDONE INF-10°. POLYPLASDONE INF-10® and POLYPLASDONE XL-10® are chemically identical materials, but have different particle size distributions, about 11 μm and about 30 μm, respectively.

Pravastatin sodium and polyplasdone were mixed in the dry state for 15 minutes and then magnesium stearate was added and the whole mixture was mixed for a further 5 minutes. Tablets were pressed from the mixture, each weighing approximately 150 mg. The pH of an aqueous dispersion of these tablets was 7.4.

Upon subjecting the so-formed tablets to a PVDC/PVC blister stability study at 40° C./75% relative humidity for 6 months, it was found that the tablets, including the pravastatin, remained substantially stable based on the weight percentage of lactone formation. The results of the stability study are presented in the table below.

| Time (months) | 0 | 1 | 2 | 3 | 4 | 6 |
|---|---|---|---|---|---|---|
| Assay, % | 103.6 | 103.4 | 100.4 | 102.7 | 100.6 | 100.5 |
| Lactone, % | 0.0 | 0.2 | 0.2 | 0.2 | 0.3 | 0.5 |

Example 2

A pravastatin formulation in the form of tablets having the following composition was prepared as described below

| Ingredient | Percent By Weight |
|---|---|
| Pravastatin Sodium | 10.0 |
| Crospovidone | 12.0 |
| Lactose Spray Dried | 77.0 |
| Magnesium Stearate | 1.00 |

Pravastatin sodium and polyplasdone were premixed and sieved, lactose spray dried was added and the materials were mixed in a dry state for 20 minutes, then magnesium stearate was added and the whole mixed for a further 5 minutes. Tablets for all strengths were pressed from the mixture. Tablet weight for 10 mg strength was approximately 100 mg, for 20 mg strength approximately 200 mg, and for 40 mg strength approximately 400 mg. The pH of the aqueous dispersion was 7.0.

Upon subjecting the so-formed tablets to a PVDC/PVC blister stability study at 40° C./75% relative humidity for 3 months, it was found that the tablets, including the pravastatin, remained substantially stable based on the weight percentage of lactone formation. The results of the stability study are presented in the table below:

| Time (months) | 0 | 1 | 2 | 3 |
|---|---|---|---|---|
| Assay, % | 98.7 | 98.7 | 100.4 | 97.5 |
| Lactone, % | 0.0 | 0.3 | 0.4 | 0.5 |

Example 3

A pravastatin formulation in the form of tablets having the following composition was prepared as described in Example 2.

| Ingredient | Percent By Weight |
|---|---|
| Pravastatin Sodium | 10.0 |
| Crospovidone | 40.0 |
| Lactose Spray Dried | 49.0 |
| Magnesium Stearate | 1.00 |

Upon subjecting the so-formed tablets to a PVDC/PVC blister stability study at 40° C./75% relative humidity for 6 months, it was found that the tablets, including the pravastatin, remained substantially stable based on the weight percentage of lactone formation. The results of the stability study are presented in the table below:

| Time (months) | 0 | 1 | 2 | 3 | 4 | 6 |
|---|---|---|---|---|---|---|
| Assay, % | 99.6 | 98.8 | 101.9 | 100.5 | 97.7 | 97.1 |
| Lactone, % | 0.0 | 0.3 | 0.4 | 0.6 | 0.5 | 0.8 |

Example 4

A pravastatin formulation in the form of 100 mg tablets having the following composition was prepared as described below.

| Ingredient | Percent By Weight |
|---|---|
| Pravastatin Sodium | 10.0 |
| Crospovidone | 60.0 |
| Microcrystalline Cellulose | 29.0 |
| Magnesium Stearate | 1.00 |

Pravastatin sodium and polyplasdone were premixed and sieved. Microcrystalline cellulose was added and the materials were mixed in a dry state for 15 minutes, then magnesium stearate was added and the whole mixed for a further 5 minutes. Tablets were pressed from the mixture. Tablet weight for 10 mg strength was approximately 100 mg. The pH of the aqueous dispersion was approximately 7.0.

Upon subjecting the so-formed tablets to a PVDC/PVC blister stability study at 40° C./75% relative humidity for 6 months, it was found that the tablets, including the pravastatin, remained substantially stable based on the weight percentage of lactone The results of the stability study are presented in the table below:

| Time (months) | 0 | 1 | 2 | 6 |
|---|---|---|---|---|
| Assay, % | 101.8 | 101.2 | 103.1 | 96.1 |
| Lactone, % | 0.0 | 0.6 | 1.0 | 2.8 |

Example 5

An atorvastatin formulation in the form of 100 mg tablets having the following composition was prepared as described below.

| Ingredient | Percent By Weight |
|---|---|
| Atorvastatin Calcium Trihydrate | 10.84 |
| Crospovidone | 40.00 |
| Lactose Spray Dried | 48.16 |
| Magnesium Stearate | 1.00 |

Atorvastatin calcium trihydrate and polyplasdone were premixed and sieved. The lactose spray dried was added and the materials were mixed in a dry state for 10 minutes. Magnesium stearate was then added and the whole mixed for a further 5 minutes. Tablets were pressed from the mixture. Tablet weight for 10 mg strength was approximately 100 mg. The pH of the aqueous dispersion was 5.4.

Upon subjecting the so-formed tablets to a PVDC/PVC blister stability study at 40° C./75% relative humidity for 3 months, it was found that the tablets, including the atorvastatin calcium, remained substantially stable based on the weight percentage of lactone formation. The results of the stability study are provided in the table below:

| Time (months) | 0 | 1 | 2 | 3 |
|---|---|---|---|---|
| Assay, % | 94.6 | 92.3 | 89.1 | 93.1 |
| Lactone, % | 0.33 | 0.31 | 0.45 | 0.45 |

Example 6

A pravastatin sodium formulation in the form of 10 mg tablets having the following composition was prepared as described below.

| Ingredient | Percent By Weight |
|---|---|
| Pravastatin Sodium | 10.0 |
| Povidone (PVP K-30) | 40.00 |
| Lactose Spray Dried | 48.16 |
| Magnesium Stearate | 1.00 |

The povidone (polyvinylpyrrolidone) used in Example 6 is commercially available from the BASF Corporation under the tradename KOLLIDON K-30.

Pravastatin sodium, lactose spray dried and povidone were premixed and sieved. These components were mixed in the dry state for about 15 minutes, after which magnesium stearate was added and further mixing conducted for about 5 minutes. Tablets were then pressed from the mixture. The approximate weight for a tablet containing 10 mg of pravastatin sodium was about 100 mg. The pH of an aqueous dispersion was approximately 6.6.

Upon subjecting the so-formed tablets to a PVDC/PVC blister stability study at 40° C./75% relative humidity for 3 months, it was found that the tablets, including the pravastatin, remained substantially stable based on the weight percentage of lactone formation. The results of the stability study are provided in the table below:

| Time (months) | 0 | 1 | 3 |
|---|---|---|---|
| Assay, % | 98.5 | 92.2 | 91.4 |
| Lactone, % | 0.0 | 1.5 | 2.8 |

Example 7

A pravastatin sodium formulation in the form of 10 mg tablets having the following composition was prepared as described below.

| Ingredient | Percent By Weight |
|---|---|
| Pravastatin Sodium | 10.0 |
| Cholestyramine (Diolite AP 143/1093) | 40.0 |

-continued

| Ingredient | Percent By Weight |
|---|---|
| Lactose Spray Dried | 49.0 |
| Magnesium Stearate | 1.0 |

Pravastatin sodium, lactose spray dried and cholestyramine were premixed and sieved. These components were mixed in the dry state for about 15 minutes, after which magnesium stearate was added and further mixing conducted for about 5 minutes. Tablets were then pressed from the mixture. The approximate weight for a tablet containing 10 mg of pravastatin sodium was about 100 mg. The pH of an aqueous dispersion was approximately 6.6.

Upon subjecting the so-formed tablets to a PVDC/PVC blister stability study at 40° C./75% relative humidity for 3 months, it was found that the tablets, including the pravastatin, remained substantially stable based on the weight percentage of lactone formation. The results of the stability study are provided in the table below:

| Time (months) | 0 | 1 | 3 |
|---|---|---|---|
| Assay, % | 97.3 | 94.2 | 91.8 |
| Lactone, % | 0.0 | 0.5 | 0.9 |

Example 8

An atorvastatin calcium formulation in the form of 10 mg tablets having the following composition was prepared as described below.

| Ingredient | Percent By Weight |
|---|---|
| Atorvastatin Calcium | 7.0 |
| Crospovidone (POLYPLASDONE XL-10) | 20.0 |
| Lactose Monohydrate | 66.4 |
| Povidone (PVP K-30) | 3.3 |
| Polysorbate 80 | 3.3 |
| Alcohol 95% process solvent | |

Atorvastatin calcium, crospovidone, lactose monohydrate and povidone were premixed and granulated using an alcohol solution of the polysorbate 80. The granulate was then milled after which tablets were pressed from the milled granulate. The approximate weight for a tablet containing 10 mg of atorvastatin calcium was about 150 mg. The pH of an aqueous dispersion was approximately 6.6.

Upon subjecting the so-formed tablets to a PVDC/PVC blister stability study at 40° C./75% relative humidity for 2 months, it was found that the tablets, including the atorvastatin calcium, remained substantially stable based on the weight percentage of lactone formation. The results of the stability study are provided in the table below:

| Time (months) | 0 | 1 | 2 |
|---|---|---|---|
| Assay, % | 97.6 | 97.0 | 94.1 |
| Lactone, % | 0.6 | 0.4 | 0.7 |

Although certain presently preferred embodiments of the invention have been described herein, it will be apparent to those skilled in the art to which the invention pertains that variations and modifications of the described embodiments may be made without departing form the spirit and scope of the invention. Accordingly, it is intended that the invention be limited only to the extent required by the appended claims and the applicable rules of law.

What is claimed is:

1. A stabilized pharmaceutical composition for the treatment of dyslipidemia, comprising an active component consisting essentially of one or more compounds selected from the group consisting of (i) a*n HMG-CoA reductase inhibiting* ring-opened 7-substituted-3,5-dihydroxyheptafloic acid or a pharmaceutically acceptable acid salt thereof, and (ii) a*n HMG-CoA reductase inhibiting* ring-opened 7-substituted-3,5-dihydroxyheptenoic acid or a pharmaceutically acceptable acid salt thereof, and a stabilizing effective amount of at least one amido-group containing polymeric compound or at least one amino-group containing polymeric compound, or combination thereof, wherein said stabilized pharmaceutical composition does not contain a stabilizing effective amount of another stabilizer or a combination of other stabilizers.

2. The composition of claim 1 wherein the at least one amido-group containing polymeric compound or at least one amino-group containing polymeric compound, or combination thereof, comprises between about 10 and about 99 percent by weight of the composition.

3. The composition of claim 2 wherein the at least one amido-group containing polymeric compound or at least one amino-group containing polymeric compound, or combination thereof, comprises between about 30 and about 80 percent by weight of the composition.

4. The composition of claim 1 wherein the active component comprises between about 0.05 and about 70 percent by weight of the composition.

5. The composition of claim 4 wherein the active component comprises between about 1 and about 60 percent by weight of the composition.

6. The composition of claim 1 wherein the active component is a pharmaceutically acceptable acid salt of pravastatin.

7. The composition of claim 6 wherein the pharmaceutically acceptable acid salt is pravastatin sodium.

8. The composition of claim 1 wherein the active component is a pharmaceutically acceptable acid salt of atorvastatin.

9. The composition of claim 8 wherein the pharmaceutically acceptable acid salt is atorvastatin calcium.

10. The composition of claim 1 wherein the composition is in the form of a solid.

11. The composition of claim 10 wherein the composition is in the form of a tablet.

12. The composition of claim 11 wherein the tablet contains a lubricant.

13. The composition of claim 12 wherein the lubricant is selected from the group consisting of magnesium stearate, sodium stearyl fumarate, polyethylene glycol, stearic acid, hydrogenated vegetable oil and talc.

14. The composition of claim 10 wherein the composition is in the form of granules.

15. The composition of claim 14 wherein the granules are constituents of a dispersion.

16. The composition of claim 10 wherein the composition is in the form of a suspension.

17. The composition of claim 10 wherein the composition is in the form of a capsule.

18. The composition of claim 10 wherein the composition is in the form of a cachet.

19. The composition of claim 1 wherein the amido group in the amido-group containing polymeric compound or the amino group in the amino-group containing polymeric compound is present either in a pendant group attached to the backbone of the polymeric compound or as a component of the backbone of the polymeric compound.

20. The composition of claim 19 wherein the amido-group containing polymeric compound is selected from the group consisting of polyvinylpyrrolidone, cross-linked polyvinylpyrrolidone, copolymers of vinylpyrrolidone and vinyl acetate, and polynoxylin.

21. The composition of claim 1, wherein the amido-group containing polymeric compound or amino-group containing polymeric compound, or combination thereof, imparts a pH of not more than about 10 to an aqueous dispersion of said composition.

22. The composition of claim 21, wherein the amido-group containing polymeric compound or amino-group containing polymeric compound, or combination thereof, imparts a pH of not more than about 8 to an aqueous dispersion of said composition.

23. The composition of claim 19, wherein the amino-group containing polymeric compound is a quaternary ammonium group-containing polymeric compound.

24. The composition of claim 23, wherein the quaternary ammonium group-containing polymeric compound is cholestyramine.

25. The composition of claim 21 wherein the ring-opened 7-substituted-3,5-dihydroxyheptanoic acid or ring-opened 7-substituted-3,5-dihydroxyheptenoic acid, or pharmaceutically acceptable acid salt thereof, is a HMG-CoA reductase inhibitor medicament that is sensitive to a low pH environment.

26. A stabilized pharmaceutical composition for the treatment of dyslipidemia comprising, in admixture, (a) an active component consisting essentially of about 0.05% to about 70% by weight of one or more compounds selected from the group consisting of (i) a*n HMG-CoA reductase inhibiting* ring-opened 7-substituted-3,5-dihydroxyheptafloic acid or a pharmaceutically acceptable acid salt thereof or (ii) a*n HMG-CoA reductase inhibiting* ring-opened 7-substituted-3,5-dihydroxyheptenoic acid or a pharmaceutically acceptable acid salt thereof, and (b) about 30% to about 99% by weight of a stabilizing effective amount of an amido-group containing polymeric compound or a stabilizing effective amount of an amino-group containing polymeric compound, or combination thereof; wherein said stabilized pharmaceutical composition does not contain a stabilizing effective amount of another stabilizer or a combination of other stabilizers.

27. The composition of claim 26, wherein the ring-opened 7-substituted 3,5-dihydroxy heptanoic acid salt is pravastatin sodium.

28. The composition of claim 26, wherein the ring-opened 7-substituted 3,5-dihydroxy heptanoic acid salt is pravastatin sodium and the amido-group containing polymeric compound is cross-linked polyvinylpyrrolidone.

29. The composition of claim 26, wherein the ring-opened 7-substituted 3,5-dihydroxy heptanoic acid salt is pravastatin sodium and the amido-group containing polymeric compound is polyvinylpyrrolidone.

30. The composition of claim 26, wherein the ring-opened 7-substituted 3,5-dihydroxy heptanoic acid salt is pravastatin sodium and the amino-group containing polymeric compound is cholestyramine.

31. The composition of claim 26, wherein the ring-opened 7-substituted 3,5-dihydroxy heptanoic acid is atorvastatin calcium.

32. The composition of claim 26, wherein the ring-opened 7-substituted 3,5-dihydroxy heptanoic acid salt is atorvastatin calcium and the amido-group containing polymeric compound is cross-linked polyvinylpyrrolidone.

33. The composition of claim 26, wherein the ring-opened 7-substituted 3,5-dihydroxy heptanoic acid salt is atorvastatin calcium and the amido-group containing polymeric compound is polyvinylpyrrolidone.

34. The composition of claim 26, in a solid tablet dosage form which further comprises a lubricant.

35. The composition of claim 34, wherein the lubricant is magnesium stearate.

36. A stabilized pharmaceutical composition comprising an active component consisting essentially of pravastatin sodium and about 40% or greater by weight of the composition of an amido-group or amino-group containing polymeric stabilizer.

37. A stabilized pharmaceutical composition comprising an active component consisting essentially of atorvastatin calcium and about 40% or greater by weight of the composition of an amido-group or amino-group containing polymeric stabilizer.

38. A method for the treatment of dyslipidemia, comprising the step of orally administering to a patient in need of such treatment a therapeutically effective unit dosage of the pharmaceutical composition of claim 1.

39. A method for the treatment of dyslipidemia, comprising the step of orally administering to a patient in need of such treatment a therapeutically effective unit dosage of the pharmaceutical composition of claim 26.

40. The stabilized pharmaceutical composition of claim 36, wherein the amount of pravastatin sodium ranges from about 7 to about 11 percent by weight of the composition.

41. The stabilized pharmaceutical composition of claim 37, wherein the amount of atorvastatin calcium ranges from about 7 to about 11 percent by weight of the composition.

*42. A stable solid pharmaceutical composition for the treatment of dyslipidemia comprising:*

*an active component consisting essentially of one or more compounds selected from the group consisting of (a) an HMG-CoA reductase inhibiting ring-opened 7-substituted-3,5-dihydroxyheptanoic acid or a pharmaceutically acceptable acid salt thereof and (b) an HMG-CoA reductase inhibiting ring-opened 7-substituted-3,5-dihydroxyheptenoic acid or a pharmaceutically acceptable acid salt thereof, and*

*at least one pharmaceutically acceptable excipient selected from the group consisting of a lubricant, a glidant, a binder, a filler, a disintegrant, a diluent, a carrier, a colorant, a coating material, and a preservative;*

*wherein the pH of the stable composition in water, if dispersed in a concentration of 1 mg active component per 1 ml water, would be about 5.4 to about 8, and*

*wherein the composition does not contain a stabilizing effective amount of one or more buffering agents and does not contain a stabilizing effective amount of one or more basifying agents.*

*43. The stable solid pharmaceutical composition of claim 42, wherein the pH would be about 6.5 to about 8.*

*44. The stable solid pharmaceutical composition of claim 42, wherein the pH would be about 6.5 to about 7.4.*

*45. The stable solid pharmaceutical composition of claim 42, wherein the basifying agents are selected from the group consisting of inorganic alkaline salts, inorganic alkaline oxides, inorganic alkaline hydroxides, alkaline metal salts, alkaline metal oxides, and alkaline metal hydroxides.*

*46. The stable solid pharmaceutical composition of claim 42, wherein the composition does not contain a buffering agent.*

*47. A stable pharmaceutical composition for the treatment of dyslipidemia comprising an active component consisting essentially of one or more compounds selected from the group consisting of atorvastatin, pravastatin, and pharmaceutically acceptable acid salts thereof, and*

*at least one pharmaceutically acceptable excipient selected from the group consisting of a lubricant, a glidant, a binder, a filler, a disintegrant, a diluent, a carrier, a colorant, a coating material, and a preservative;*

*wherein the pH of the stable composition in water, if dispersed in a concentration of 1 mg active component per 1 ml water, would be about 5.4 to about 8, and*

*wherein the composition does not contain a stabilizing effective amount of one or more buffering agents and does not contain a stabilizing effective amount of one or more basifying agents.*

*48. The stable solid pharmaceutical composition of claim 42 or claim 47, wherein no more than about 10% of the active component initially present in the composition would degrade into the corresponding lactone if (i) tabletted, (ii) packaged in a PVDC/PVC blister package and (iii) stored for six months at 40° C. and 75% relative humidity.*

*49. The stable solid pharmaceutical composition of claim 48, wherein no more than about 5% of the active component initially present in the composition would degrade into the corresponding lactone.*

*50. The stable solid pharmaceutical composition of claim 48, wherein no more than 1% of the active component initially present in the composition would degrade into the corresponding lactone.*

*51. The stable solid pharmaceutical composition of claim 48, wherein no more than about 1% of the active component initially present in the composition would degrade into the corresponding lactone if (i) tabletted, (ii) packaged in packing equivalent to or better than a PVDC/PVC blister package and (iii) stored for six months at 40° C. and 75% relative humidity.*

*52. A stable solid pharmaceutical composition for the treatment of dyslipidemia comprising:*

*an active component consisting essentially of one or more compounds selected from the group consisting of (i) an HMG-CoA reductase inhibiting ring-opened 7-substituted-3,5-dihydroxyheptanoic acid or a pharmaceutically acceptable acid salt thereof and (ii) an HMG-CoA reductase inhibiting ring-opened 7-substituted-3,5-dihydroxyheptenoic acid or a pharmaceutically acceptable acid salt thereof, and*

*a stabilizing effective amount of a stabilizing compound, with the proviso that the composition does not contain a stabilizing effective amount of one or more buffering agents and does not contain a stabilizing effective amount of one or more basifying agents.*

*53. The stable solid pharmaceutical composition of claim 52, wherein the pH of the stable composition in water, if dispersed in a concentration of 1 mg active component per 1 ml in water, would be about 5.4 to about 8.*

*54. The composition of claim 52, wherein the active component consists essentially of one or more compounds selected from the group consisting of atorvastatin, pravastatin, fluvastatin, cerivastatin and pharmaceutically acceptable acid salts thereof.*

*55. A stable solid pharmaceutical composition for the treatment of dyslipidemia comprising:*

*an active component consisting essentially of one or more compounds selected from the group consisting of atorvastatin, pravastatin, fluvastatin, cerivastatin and pharmaceutically acceptable acid salts thereof, and*

*means for preventing degradation of the active component into the corresponding lactone,*

*wherein the pH of the stable composition in water, if dispersed in a concentration of 1 mg active component per 1 ml water, would be about 5.4 to about 8, and*

*wherein the composition does not contain a stabilizing effective amount of one or more buffering agents and does not contain a stabilizing effective amount of one or more basifying agents.*

* * * * *

UNITED STATES PATENT AND TRADEMARK OFFICE

CERTIFICATE OF CORRECTION

PATENT NO. : RE 39,502 E
APPLICATION NO. : 11/083366
DATED : March 6, 2007
INVENTOR(S) : Fox et al.

It is certified that error appears in the above-identified patent and that said Letters Patent is hereby corrected as shown below:

In col. 2, ln. 60, replace “mark LIPITOR ® is” with --mark LIPITOR ®) is--.

In col. 8, ln. 61, replace “pharmaceutical acceptable” with --pharmaceutically acceptable--.

In col. 11, ln. 53, replace “INF-10°” with --INF 10®--.

In col. 17, ln. 52, replace “7-substituted-3,5-dihydroxyheptafloic acid” with --7-substituted-3,5-dihydroxyheptanoic acid--.

Signed and Sealed this

Seventh Day of October, 2008

JON W. DUDAS
*Director of the United States Patent and Trademark Office*